US010281480B2

(12) United States Patent
Patzke

(10) Patent No.: US 10,281,480 B2
(45) Date of Patent: May 7, 2019

(54) METHOD FOR DETECTING MODULATORS OF GPIB-THROMBIN INTERACTION

(71) Applicant: Siemens Healthcare Diagnostics Products GmbH, Marburg (DE)

(72) Inventor: Juergen Patzke, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 259 days.

(21) Appl. No.: 14/643,938

(22) Filed: Mar. 10, 2015

(65) Prior Publication Data

US 2015/0260736 A1  Sep. 17, 2015

(30) Foreign Application Priority Data

Mar. 11, 2014  (EP) .................... 14158716

(51) Int. Cl.
*G01N 33/53*  (2006.01)
*G01N 33/86*  (2006.01)

(52) U.S. Cl.
CPC ....... *G01N 33/86* (2013.01); *G01N 2333/745* (2013.01); *G01N 2333/755* (2013.01); *G01N 2333/974* (2013.01)

(58) Field of Classification Search
None
See application file for complete search history.

(56) References Cited

U.S. PATENT DOCUMENTS

| 5,486,361 A | 1/1996 | Gralnick |
| 2010/0136589 A1 | 6/2010 | Althaus |
| 2012/0149030 A1* | 6/2012 | Mintz ................. G01N 33/86 435/7.4 |
| 2013/0230868 A1 | 9/2013 | Patzke |

FOREIGN PATENT DOCUMENTS

| CN | 1553955 A | 12/2004 |
| CN | 1823090 A | 8/2006 |
| CN | 102279273 A | 12/2011 |
| CN | 102993307 A | 3/2013 |
| DE | 102007031708 A1 | 1/2009 |
| EP | 0515194 A2 | 11/1992 |
| EP | 2637024 A1 | 9/2013 |
| JP | 2010-532467 A | 10/2010 |
| JP | 2013-186124 A | 9/2013 |
| WO | WO 9506877 A1 | 3/1995 |
| WO | WO2009/007051 A2 | 1/2009 |
| WO | WO 2009026551 A1 | 2/2009 |

OTHER PUBLICATIONS

Mazurov et al., (Thrombosis Research 1991, 62;673-684).*
Pontiggia et al, 2006, Thrombosis and Haemostasis, 96/6 (Dec) pp. 697-863.*
Anderson et al., Molecular and Cellular Proteomics 2002;1:845-867 see p. 846, right column and whole article.*
Lopez, J.A. et al., Cloning of the alpha chain of human platelet glycoprotein lb: a transmembrane protein with homology to leucine-rich alpha2-glycoprotein. Proc. Natl. Acad. Sci., USA, 1987, 84, 5615-5619.; 1987; US.
Ruan, C. et al., A murine antiglycoprotein lb complex monoclonal antibody, SZ 2, inhibits platelet aggregation induced by both ristocetin and collagen. Blood, 1987, 69(2): 570-577.; 1987.
Beer, J.H. et al., Glycocalicin: A New Assay—The Normal Plasma Levels and Its Potential Usefulness in Selected Diseases. Blood 1994, 83(3): 691-702; 1994.
Firbas, C. et al., Targeting von Willebrand factor and platelet glycoprotein lb receptor. Expert Rev. Cardiovasc. Ther. 2010, 8(12): 1689-1701; 2010.
De Candia, E., Mechanisms of platelet activation by thrombin: A short history. Thrombosis Research 2012, 129: 250-256.; 2012; IT.
Ward, C.M. et al., Mocarhagin, a novel cobra venom metalloproteinase, cleaves the platelet von Willebrand factor receptor glycoprotein lb. Identification of the sulfated tyrosine/anionic sequence Tyr-276-Glu-282 of glycoprotein lb as a binding site for von Willebrand factor and -thrombin. Biochemistry 1996, 35: 4929-4938.; 1996; AU.
Ruggeri, Z.M. et al., Unravelling the mechanism and significance of thrombin binding to platelet glycoprotein lb. Thrombosis and Haemostasis 2010, 104.5: 894-902.
Yeung, J. & Holinstat, M., Newer agents in antiplatelet therapy: a review. Journal of Blood Medicine 2012, 3: 33-42.
Dubois, C. et al., Thrombin binding to GPIba induces integrin alphaIIbβ3 dependent platelet adhesion to fibrin in ex vivo lowing whole blood. Thromb Haemost 2004, 91: 233-237.
Othman M. et al; "Platelet-Type von Willebrand Disease: New Insights into the Molecular Pathophysiology of a Unique Platelet Defect"; Seminars in Thrombosis and Hemostasis; vol. 39; No. 6; pp. 663-673; XP002728599; 2013.
Shen Yang et al; "Functional analysis of the C-terminal flanking sequence of platelet glycoprotein lba using canine-human chimeras"; Hemostasis, Thrombosios, ans Vascular Biology, Blood; vol. 99; No. 1; pp. 145-150; ISSN: 0006-4971; XP002728598; 2002; Jan. 1, 2002.
Pozzi N.; "Struttura e Funzione dei Fattori della Coagulazione"; Universita degli studi die Padova; URL: http://paduaresearch.cab.unipd.it/2395/1/Ph.D._Thesis_-_Nicola_pozzi_21/01/2010.pdf, pp. 1-202; XP002728597; 2010; Jan. 21, 2010, (submitting in 2 parts).
European Search Report of European Patent Application No. EP14158716 dated Sep. 17, 2014.
Japanese Office Action of Japanese Application No. 2015-046610 dated May 15, 2018.
Chinese Search Report of Chinese Application No. 201510102598X dated Aug. 28, 2017.

* cited by examiner

*Primary Examiner* — Tracy Vivlemore
*Assistant Examiner* — Carmencita M Belei
(74) *Attorney, Agent, or Firm* — Dugan & Dugan, PC

(57) ABSTRACT

The present invention is in the field of coagulation diagnostics and relates to methods for detecting modulators of GPIb-thrombin interaction in a sample. To this end, the sample is contacted with isolated mutated GPIbα protein and thrombin, and the formation of a complex between mutated GPIbα protein and thrombin is determined.

4 Claims, 1 Drawing Sheet

Specification includes a Sequence Listing.

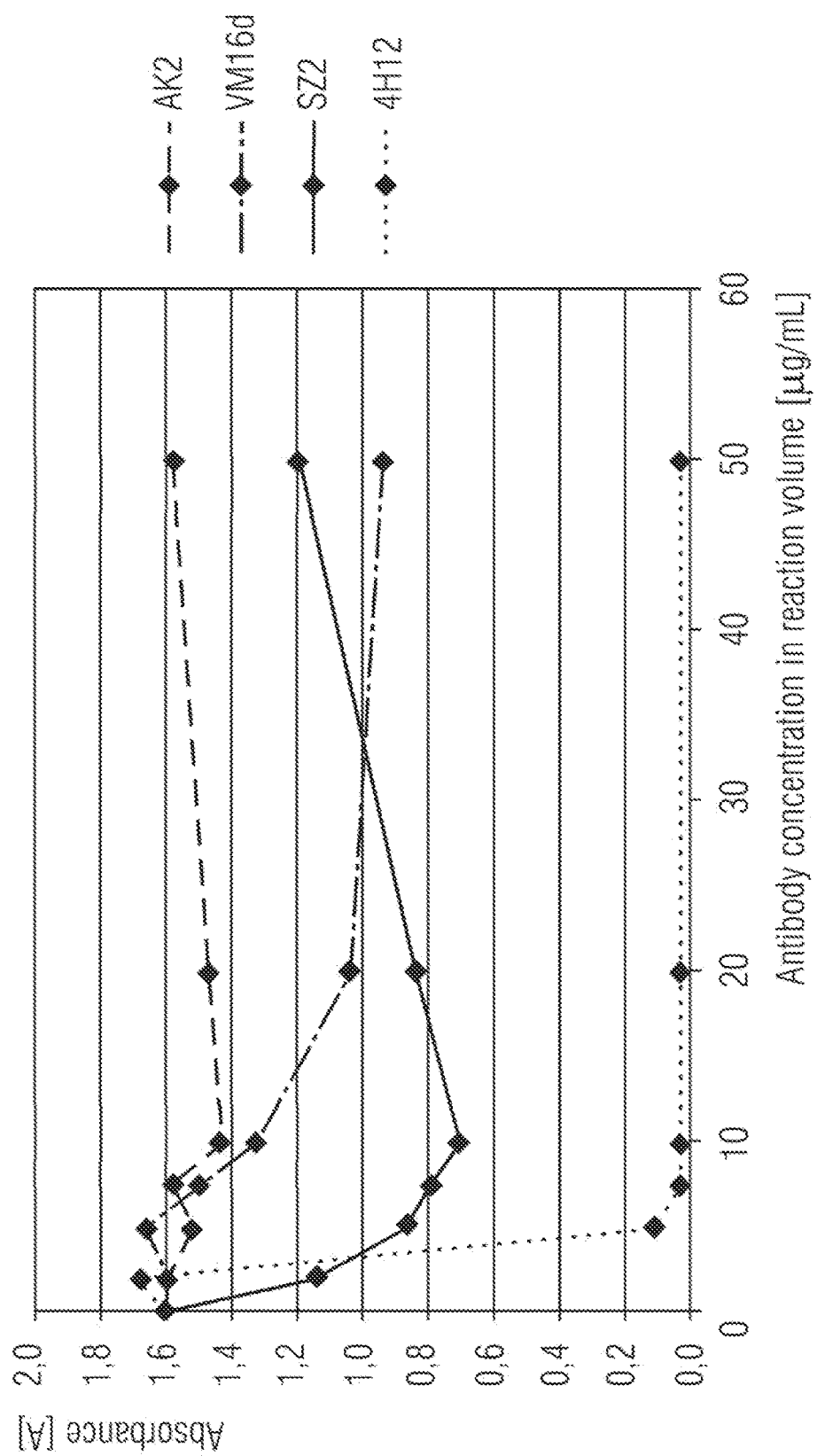

SEQUENCE LISTING

```
<160> NUMBER OF SEQ ID NOS: 3

<210> SEQ ID NO 1
<211> LENGTH: 610
<212> TYPE: PRT
<213> ORGANISM: Homo sapiens

<400> SEQUENCE: 1

His Pro Ile Cys Glu Val Ser Lys Val Ala Ser His Leu Glu Val Asn
1               5                   10                  15

Cys Asp Lys Arg Asn Leu Thr Ala Leu Pro Pro Asp Leu Pro Lys Asp
            20                  25                  30

Thr Thr Ile Leu His Leu Ser Glu Asn Leu Leu Tyr Thr Phe Ser Leu
        35                  40                  45

Ala Thr Leu Met Pro Tyr Thr Arg Leu Thr Gln Leu Asn Leu Asp Arg
    50                  55                  60
```

```
Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                     85                  90                  95

Gln Thr Leu Pro Ala Leu Thr Val Leu Asp Val Ser Phe Asn Arg Leu
                100                 105                 110

Thr Ser Leu Pro Leu Gly Ala Leu Arg Gly Leu Gly Glu Leu Gln Glu
                115                 120                 125

Leu Tyr Leu Lys Gly Asn Glu Leu Lys Thr Leu Pro Pro Gly Leu Leu
            130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
                180                 185                 190

Gly Ser His Leu Leu Pro Phe Ala Phe Leu His Gly Asn Pro Trp Leu
            195                 200                 205

Cys Asn Cys Glu Ile Leu Tyr Phe Arg Arg Trp Leu Gln Asp Asn Ala
210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
                260                 265                 270

Thr Asp Leu Tyr Asp Tyr Tyr Pro Glu Glu Asp Thr Glu Gly Asp Lys
            275                 280                 285

Val Arg Ala Thr Arg Thr Val Val Lys Phe Pro Thr Lys Ala His Thr
290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                325                 330                 335

Thr Thr Phe Pro Pro Arg Trp Thr Pro Asn Phe Thr Leu His Met Glu
                340                 345                 350

Ser Ile Thr Phe Ser Lys Thr Pro Lys Ser Thr Thr Glu Pro Thr Pro
            355                 360                 365

Ser Pro Thr Thr Ser Glu Pro Val Pro Glu Pro Ala Pro Asn Met Thr
370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Pro Ile Pro Thr Ile
                405                 410                 415

Ala Thr Ser Pro Thr Ile Leu Val Ser Ala Thr Ser Leu Ile Thr Pro
                420                 425                 430

Lys Ser Thr Phe Leu Thr Thr Thr Lys Pro Val Ser Leu Leu Glu Ser
                435                 440                 445

Thr Lys Lys Thr Ile Pro Glu Leu Asp Gln Pro Pro Lys Leu Arg Gly
            450                 455                 460

Val Leu Gln Gly His Leu Glu Ser Ser Arg Asn Asp Pro Phe Leu His
465                 470                 475                 480
```

-continued

```
Pro Asp Phe Cys Cys Leu Leu Pro Leu Gly Phe Tyr Val Leu Gly Leu
              485                 490                 495

Phe Trp Leu Leu Phe Ala Ser Val Val Leu Ile Leu Leu Leu Ser Trp
        500                 505                 510

Val Gly His Val Lys Pro Gln Ala Leu Asp Ser Gly Gln Gly Ala Ala
        515                 520                 525

Leu Thr Thr Ala Thr Gln Thr Thr His Leu Glu Leu Gln Arg Gly Arg
    530                 535                 540

Gln Val Thr Val Pro Arg Ala Trp Leu Leu Phe Leu Arg Gly Ser Leu
545                 550                 555                 560

Pro Thr Phe Arg Ser Ser Leu Phe Leu Trp Val Arg Pro Asn Gly Arg
                565                 570                 575

Val Gly Pro Leu Val Ala Gly Arg Arg Pro Ser Ala Leu Ser Gln Gly
            580                 585                 590

Arg Gly Gln Asp Leu Leu Ser Thr Val Ser Ile Arg Tyr Ser Gly His
        595                 600                 605

Ser Leu
    610

<210> SEQ ID NO 2
<211> LENGTH: 16
<212> TYPE: PRT
<213> ORGANISM: Homo sapiens

<400> SEQUENCE: 2

Met Pro Leu Leu Leu Leu Leu Leu Leu Pro Ser Pro Leu His Pro
1               5                   10                  15

<210> SEQ ID NO 3
<211> LENGTH: 41
<212> TYPE: PRT
<213> ORGANISM: Artificial
<220> FEATURE:
<223> OTHER INFORMATION: heterologous signal peptide

<400> SEQUENCE: 3

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg
        35                  40
```

METHOD FOR DETECTING MODULATORS OF GPIB-THROMBIN INTERACTION

CROSS-REFERENCE TO RELATED APPLICATION

This application claims priority to European Patent Application No. EP 14158716 (14158716.2), filed Mar. 11, 2014, which is hereby incorporated by reference herein in its entirety for all purposes.

This application incorporates by reference herein in its entirety the sequence listing which is submitted together with this application in computer readable form and which has the file name 2013P22440US_SEQ.txt and is 7 KB.

FIELD

The present invention is in the field of coagulation diagnostics and relates to methods for detecting modulators of GPIb-thrombin interaction in a sample.

BACKGROUND

Thrombin (factor IIa) is involved in a multiplicity of activating and inhibitory mechanisms of plasmatic blood coagulation and is thus the central enzyme of secondary hemostasis, which primarily comprises the formation of fibrin. Less well studied and understood is the role of thrombin in primary hemostasis, which comprises the activation of platelets and adhesion of platelets as a result of an endothelial injury. It is known that thrombin is a platelet activator and stimulates the aggregation of platelets. The most important thrombin receptors on the platelet surface are, firstly, the PAR receptors (protease-activated receptors) and, secondly, the glycoprotein Ib-V-IX receptor complex. The glycoprotein Ib-V-IX receptor complex comprises the integral membrane protein glycoprotein Ib (GPIb), the integral membrane protein glycoprotein IX (GPIX) and glycoprotein V (De Candia, E., Mechanisms of platelet activation by thrombin: A short history. Thrombosis Research 2012, 129: 250-256).

GPIb is a double-chain molecule consisting of a heavy chain with an apparent molecular mass of about 145 kDa (synonymous: alpha-chain or GPIbα) and a light chain with an apparent molecular mass of about 22 kDa (synonymous: beta-chain or GPIbβ), which are connected to one another via disulfide bonds (Lopez, J. A. et al., Cloning of the a chain of human platelet glycoprotein Ib: A transmembrane protein with homology to leucine-rich $α_2$-glycoprotein. Proc. Natl. Acad. Sci USA 1987, 84: 5615-5619).

The GPIbα protein contains binding sites for thrombin and thus brings about the binding of thrombin to the glycoprotein Ib-V-IX receptor complex. A fragment of the GPIbα chain is glycocalicin, which is proteolytically cleaved from the intact receptor in the platelet membrane. Glycocalicin is detectable in plasma. Elevated concentrations of free glycocalicin in plasma indicate a disruption in platelet function (Beer, J. H. et al., Glycocalicin: A New Assay—The Normal Plasma Levels And Its Potential Usefulness in Selected Diseases. Blood 1994, 83(3): 691-702).

Since thrombin and platelets play a central role in the development of arterial thromboses and since inhibitors of platelet aggregation for prophylactic and therapeutic use are meanwhile being researched and used, the specific study of the interaction of thrombin and platelets is of great interest.

It is therefore desirable to have methods which allow the detection of modulators, i.e., inhibitors or activators, of platelet-thrombin interaction in patient samples. Such methods would allow the monitoring of platelet inhibitor therapies or even the detection of physiological disruptive factors, such as, for example, activating or inhibitory autoantibodies.

SUMMARY

It is an object of the present invention to provide a method for specifically detecting modulators of GPIb-thrombin interaction in a sample.

The object is achieved by contacting the sample with isolated GPIbα protein and with isolated thrombin and determining the formation of a complex between the GPIbα protein and thrombin, the GPIbα protein being mutated and, compared to the wild-type sequence of the human GPIbα protein, containing at least the amino acid residues 1-268 and having a substitution Xaa at at least one of the positions 233, 235, 237 and 239 (SEQ ID NO: 1).

In another aspect, an assay kit for carrying out a method for detecting modulators of GPIb-thrombin interaction in a sample contains a first reagent containing isolated GPIbα protein, the GPIbα protein being mutated and, compared to the wild-type sequence of the human GPIbα protein, contains at least the amino acid residues 1-268 and has a substitution Xaa at at least one of the positions 233, 235, 237 and 239 (SEQ ID NO: 1), and a second reagent containing thrombin.

BRIEF DESCRIPTION OF THE DRAWINGS

FIG. 1 shows the absorbance measurement values [A] of reaction volumes with different anti-GPIb antibodies in different concentrations. The antibodies VM16d, SZ2 and 4H12 inhibit the thrombin-GPIb interaction in a concentration-dependent manner (see example 1).

DETAILED DESCRIPTION

The term "modulator of GPIb-thrombin interaction" encompasses substances which influence the GPIb-thrombin interaction. Inhibitors of GPIb-thrombin interaction reduce the binding of thrombin to GPIbα protein. Activators of GPIb-thrombin interaction intensify the binding of thrombin to GPIbα protein.

If the sample contains an activator, the formation of a complex is intensified compared to a standard sample.

If the sample contains an inhibitor, for example
- a therapeutically administered thrombin inhibitor, for example from the group of exosite I inhibitors (e.g., hirudin) or exosite II inhibitors (e.g., heparin) (Ruggeri, Z. M. et al., Unravelling the mechanism and significance of thrombin binding to platelet glycoprotein Ib. Thrombosis and Haemostasis 2010, 104.5: 894-902) or
- a physiological thrombin inhibitor, such as, for example, autoantibodies against thrombin, which prevent the binding of thrombin to GPIbα, or
- a therapeutic administered GPIbα inhibitor, such as, for example, an anti-GPIbα antibody, for example the antibody 4H12 (U.S. Pat. No. 5,486,361 A) or the antibody SZ2 (Ruan, C. et al., A murine antiglycoprotein Ib complex monoclonal antibody, SZ 2, inhibits platelet aggregation induced by both ristocetin and collagen. Blood 1987, 69(2): 570-577) or H6B4-Fab, the Fab fragment of a humanized monoclonal anti-GPIbα antibody (Firbas, C. et al., Targeting von Willebrand factor and platelet glycoprotein Ib receptor.

Expert Rev. Cardiovasc. Ther. 2010, 8(12): 1689-1701), or GPG-290, a recombinant, chimeric antibody containing the amino-terminal amino acids 1-290 of GPIbα coupled to human IgG1 (Yeung, J. & Holinstat, M., Newer agents in antiplatelet therapy: a review. Journal of Blood Medicine 2012, 3: 33-42), or a physiological GPIbα inhibitor, such as, for example, autoantibodies against GPIbα, which prevent the binding of GPIbα to thrombin, or elevated glycocalicin concentrations, which compete with the GPIbα protein for binding to thrombin, the formation of a complex is reduced compared to a standard sample.

The present invention therefore provides a method for detecting modulators of GPIb-thrombin interaction in a sample, the sample being contacted with isolated GPIbα protein and with isolated thrombin and the formation of a complex between the GPIbα protein and thrombin being determined. The GPIbα protein used is mutated and, compared to the wild-type sequence of the human GPIbα protein, contains at least the amino acid residues 1-268 and has a substitution Xaa at at least one of the positions 233, 235, 237 and 239 (SEQ ID NO: 1).

It is advantageous that said method manages without the use of platelets. The preparation of platelet reagents from animal or human blood is costly and inconvenient and does not guarantee a consistent quality.

The term "sample" encompasses biological liquids particularly from humans and animals, such as blood, plasma or serum.

The term "standard sample" encompasses a reference material which, when used as a sample in the method according to the invention, generates a measurement value corresponding to the GPIb-thrombin interaction of a healthy individual or of a healthy population of individuals, which individual or which population does not have a GPIb-thrombin interaction influenced by a modulator of GPIb-thrombin interaction. A suitable reference material is, for example, a pool composed of a body fluid, for example a standard plasma pool or standard serum pool, from generally at least 20 clearly healthy individuals.

The GPIbα protein used in the method according to the invention can be a recombinantly or synthetically produced GPIbα protein. Suitable for the production of recombinant GPIbα protein are known prokaryotic or eukaryotic expression systems, such as, for example, the expression in bacteria (e.g., *E. coli*), in yeasts (e.g., *Saccharomyces cerevisiae, Pichia pastoris*), in plant, animal or human cell cultures. Suitable for the production of synthetic GPIbα protein are known techniques for in vitro protein synthesis, such as, for example, solid-phase syntheses (e.g., Merrifield synthesis). Preferably, the GPIbα protein used in the method according to the invention is recombinantly produced GPIbα protein which was produced in a culture of human cells, preferably in a culture of human embryonic kidney cells (HEK cells).

Preferably, the GPIbα protein is added to the assay volume in such an amount that a final concentration of 0.5-50 μg/mL GPIbα in the assay volume, particularly preferably of 1-10 μg/mL GPIbα in the assay volume, very particularly preferably of 5 μg/mL GPIbα in the assay volume, is obtained.

The GPIbα protein used in the method according to the invention can, at the N-terminus, be fused to the homologous human GPIbα signal sequence MPLLLLLLLL-PSPLHP (SEQ ID NO: 2, also referred to as amino acid residues −16 to −1). Alternatively, the GPIbα protein used can, at the N-terminus, be fused to a heterologous signal sequence, i.e., to a polypeptide not usually present in the human GPIbα polypeptide, which signal sequence, however, positively influences the expression and/or secretion of the recombinantly expressed GPIbα protein in the selected expression system. A suitable heterologous signal sequence is, for example, MPLQLLLLLILLGPGNSLQLWDT-WADEAEKALGPLLARDRR (SEQ ID NO: 3).

Furthermore, the GPIbα protein used in the method according to the invention can, at the C-terminus, be fused to one or more affinity tags which allow the binding of the, for example, recombinantly expressed protein to an affinity support, allowing, for example, the purification of recombinantly expressed GPIbα protein. Preference is given to small affinity tags having a length of not more than 12 amino acids. Particular preference is given to affinity tags from the group consisting of His-tag, Flag-tag, Arg-tag, c-Myc-tag and Strep-tag. Suitable affinity supports which bind with high affinity to an affinity tag are, for example, specific antibodies, immobilized cations (e.g., $Ni^{2+}$ with affinity for His-tags) or other types of binding partners (e.g., streptavidin with affinity for Strep-tags).

The isolated GPIbα protein used is mutated and—compared to the wild-type sequence of the human GPIbα protein (SEQ ID NO: 1)—contains at least the amino acid residues 1-268 and a substitution Xaa at at least one of the positions 233, 235, 237 and 239. Preferably, the mutated GPIbα protein contains a substitution Xaa in each case at two of the positions 233, 235, 237 and 239. It was found that, surprisingly, the use of wild-type GPIbα protein is not suitable for the detection of modulators of GPIb-thrombin interaction.

Preferably, the substitutions Xaa of the glycine residue at position 233 and of the methionine residue at position 239 of the GPIbα chain consist of a valine residue (G233V and M239V) or a serine residue (G233S and M239S). Any desired combination of different substitutions Xaa at the two positions is possible. Particular preference is given to the combination G233V/M239V. The substitution Xaa of the aspartic acid residue at position 235 preferably consists of a tyrosine residue (D235Y). The substitution Xaa of the lysine residue at position 237 preferably consists of a valine residue (K237V). The stated mutations are gain-of-function mutations which are known to have a significantly higher affinity for VWF and interact more strongly with VWF than wild-type GPIbα protein. Neither ristocetin, botrocetin nor a ristocetin-equivalent substance is added to the assay volume.

The thrombin used in the method according to the invention can be recombinant human or bovine thrombin, or human or bovine thrombin isolated from natural sources.

In a preferred embodiment of the method according to the invention, the thrombin and/or the GPIbα protein is associated with a solid phase.

The term "associated" can be broadly comprehended and encompasses, for example, a covalent and a noncovalent bond, a direct and an indirect bond, the adsorption to a surface and the containment in a recess. In the case of a covalent bond, the isolated GPIbα protein is bonded to the solid phase via a chemical bond. An example of a noncovalent bond is surface adsorption. Besides a direct bond to the solid phase, the isolated GPIbα protein or the thrombin can also be indirectly bonded to the solid phase via a specific interaction with other specific binding partners, for example via a specific interaction with an antibody or an antibody fragment, preferably with an anti-GPIbα antibody or with an anti-thrombin antibody or—if the isolated protein has an affinity tag—with an anti-affinity-tag antibody.

In the context of this invention, the term "solid phase" includes an article which consists of porous and/or nonporous, water-insoluble material and can have a very wide variety of different forms such as, for example, vessel, tube, microtitration plate (ELISA plate), bead, microparticle, rod, strip, filter or chromatography paper, etc. Generally, the surface of the solid phase is hydrophilic or can be made hydrophilic. The solid phase can consist of a very wide variety of different materials such as, for example, of organic and/or of inorganic materials, of synthetic materials, of naturally occurring materials and/or of modified naturally occurring materials. Examples of solid-phase materials are polymers such as, for example, cellulose, nitrocellulose, cellulose acetate, polyvinyl chloride, polyacrylamide, cross-linked dextran molecules, agarose, polystyrene, polyethylene, polypropylene, polymethacrylate or nylon; latex; ceramics; glass; metals, in particular noble metals such as gold and silver; magnetite; mixtures or combinations of the same. The term "solid phase" explicitly does not encompass cells, in particular platelets (thromobocytes). Thus, in any case, the solid phase is a nonthrombocytic solid phase.

The solid phase can have a coating composed of one or more layers, for example composed of proteins, carbohydrates, lipophilic substances, biopolymers, organic polymers or mixtures thereof, in order, for example, to suppress or prevent the nonspecific binding of sample constituents to the solid phase or in order, for example, to achieve improvements with respect to the suspension stability of particulate solid phases, with respect to storage stability, with respect to shape-giving stability or with respect to resistance against UV light, microbes or other destructively acting agents.

Contacting of isolated GPIbα protein with thrombin leads to the formation of a complex composed of the two components. If the patient sample which is added contains substances which influence said complex formation, for example GPIb or thrombin inhibitors or GPIb or thrombin activators, a complex formation which is altered with respect to the standard is measured. The standard is determined by determining the GPIb-thrombin interaction in suitable reference materials, for example in a standard plasma pool, and can, for example, be defined as 100% of the norm. The GPIb-thrombin interaction which is determined in a sample from an individual can then be set in relation to the reference value.

In one embodiment of the method according to the invention, at least one of the two components, i.e., GPIbα and/or thrombin, is associated with a particulate solid phase, preferably with latex particles. The formation of a complex between thrombin, GPIbα protein and the associated solid phase(s) can then be determined by measuring the agglutination of the particulate solid phase. To quantitatively determine the agglutination reaction, which correlates with the formation of a complex, use can be made of, for example, light scattering on the particle aggregates via the measurement of scattered light intensity (nephelometry) or via the measurement of turbidity of the medium (turbidimetry).

In another embodiment of the method according to the invention, each of the two components, i.e., GPIbα and thrombin, is or becomes associated with a first and a second component of a signal-forming system, which cooperate in such a way that a detectable signal is produced when the first and the second component of the signal-forming system are brought into close proximity with one another. A cooperation between the components is to be understood in particular to mean an energy transfer, i.e., the direct transfer of energy between the components, for example by means of light radiation or electron radiation and also via reactive chemical molecules, such as, for example, short-lived singlet oxygen. The energy transfer can take place from one component to another component; however, another possibility is a cascade of different substances, via which the energy transfer proceeds. For example, the components can be a pair composed of an energy donor and an energy recipient, such as, for example, photosensitizer and chemiluminescent agent (EP-A2-0515194, LOCI® technology) or photosensitizer and fluorophore (WO-A1-95/06877) or radioactive iodine<125> and fluorophore, or fluorophore and fluorescence quencher.

In another embodiment of the method according to the invention, the thrombin is associated with a nonparticulate solid phase, preferably with the surface of a microtiter plate. The formation of a complex between thrombin and GPIbα protein can then be determined by measuring the amount of GPIbα which is bound to the solid phase via the thrombin. To determine the amount of GPIbα which has been bound to the solid phase via the thrombin, it is, for example, possible to use an anti-GPIbα antibody which is directly or indirectly associated with a component of a signal-forming system and thus allows the quantification of the amount of GPIbα bound. Alternatively, the GPIbα protein can be associated with a nonparticulate solid phase, and the formation of a complex between thrombin and GPIbα protein can be determined by measuring the amount of thrombin which is bound to the solid phase via the GPIbα protein. To determine the amount of thrombin which has been bound to the solid phase via the GPIbα, it is, for example, possible to use an anti-thrombin antibody which is directly or indirectly associated with a component of a signal-forming system or a peptide substrate having a thrombin-cleavable signal group, for example a chromogenic, fluorogenic or electrogenic signal group.

The present invention further provides an assay kit for carrying out a method according to the invention, containing a first reagent containing isolated GPIbα protein, the GPIbα protein being mutated and, compared to the wild-type sequence of the human GPIbα protein, containing at least the amino acid residues 1-268 and having a substitution Xaa at at least one of the positions 233, 235, 237 and 239 (SEQ ID NO: 1), and a second reagent containing thrombin. Particular preference is given to an assay kit containing a reagent containing isolated, mutated GPIbα protein which has a substitution Xaa in each case at at least two of the positions 233, 235, 237 and 239, particularly preferably at the positions 233 and 239. Very particularly preferably, the substitutions Xaa of the glycine residue at position 233 and of the methionine residue at position 239 of the GPIbα chain consist of a valine residue (G233V and M239V). Another preferred assay kit contains a reagent containing isolated, mutated GPIbα protein which has a substitution Xaa in each case at the positions 233, 235 and 239. Preferably, the substitutions Xaa of the glycine residue at position 233 and of the methionine residue at position 239 of the GPIbα chain consist of a valine residue (G233V and M239V) or a serine residue (G233S and M239S) and the substitution Xaa of the aspartic acid residue at position 235 consists of a tyrosine residue (D235Y).

In one embodiment of the assay kit, the second reagent can comprise a solid phase to which the thrombin is associated. Preferably, such an assay kit further contains one further reagent or two or more further reagents for detecting the isolated GPIbα protein, containing, for example, an anti-GPIbα antibody or an anti-Tag antibody which is directly or indirectly labeled with an enzyme and a substrate for the enzyme, for example a horseradish peroxidase-labeled antibody and the chromogenic substrate tetramethylbenzidine.

In another embodiment of the assay kit, the first reagent can comprise a solid phase to which the mutated GPIbα protein is associated. Preferably, such an assay kit further contains one further reagent or two or more further reagents for detecting thrombin, containing, for example, an anti-thrombin antibody which is directly or indirectly labeled with an enzyme and a substrate for the enzyme, for example a horseradish peroxidase-labeled antibody and the chromogenic substrate tetramethylbenzidine. Alternatively, it is also possible to use a peptide substrate having a thrombin-cleavable signal group in order to detect thrombin.

The reagents can be provided in liquid or lyophilized form. If a reagent is present as a lyophilisate, the assay kit can additionally contain a solvent required for suspending the lyophilisate, such as, for example, distilled water or a suitable buffer.

EXAMPLES

Example 1: Detection of Inhibitory GPIb Antibodies in a Sample

A microtiter plate was coated with antibodies against human thrombin. Human thrombin was obtained from Sigma-Aldrich (T7009, Sigma-Aldrich, Hamburg, Germany). 100 µL of a solution of 1 µg/mL thrombin in glycerol buffer (8 mL of distilled water, 87.7 mg of NaCl, 69 mg of $NaH_2PO_4*H_2O$, 813 µL of 87% strength glycerol, 18 µL of Tween® 20, 10 mg of bovine albumin, 1 mg of bovine IgG, 2 mg of phenol, 18.6 mg of Titriplex I, adjusted to pH 6.8 with ca. 43 µL of 10 N NaOH) were added to each well and incubated for one hour at room temperature. This was followed by washing four times with 300 µL of wash buffer.

Use was made of a recombinantly produced, Flag-tag-fused GPIbα protein (aa 1-268) in which the glycine residue at position 233 and the methionine residue at position 239 is replaced in each case by a valine residue (G233V, M239V). From this GPIbα protein, 200 µL of a 10 µg/mL solution in glycerol buffer were mixed in each case with 200 µL of the inhibitory anti-GPIbα antibodies 4H12, SZ2 and VM16D or of the control antibody AK2 in different concentrations in glycerol buffer and incubated for one hour and 10 minutes at room temperature. From these GPIbα protein/antibody mixtures, 100 µL were pipetted in each case into a well of the microtiter plate and incubated for one hour at room temperature. This was followed by washing four times with 300 µL of wash buffer.

To quantitatively detect the bound, Flag-tag-fused GPIbα protein, 100 µL of a 0.06 µg/mL solution of anti-Flag M2-peroxidase (Sigma-Aldrich, Hamburg, Germany) in glycerol buffer were added in each case to each well and incubated for one hour at room temperature. After washing four times with 300 µL of wash buffer, 100 µL of a solution of the chromogenic peroxidase substrate TMB (tetramethylbenzidine dihydrochloride) and hydrogen peroxide were added to each well and incubated for 20 minutes. The reaction was stopped, and the absorbance of the reaction volumes was measured with light at a wavelength of 450 nm in an ELISA plate reader using a reference wavelength of 650 nm.

The absorbance measurement values are shown in FIG. 1.

The anti-GPIb antibody AK2 was used as control antibody, which is known not to influence the binding of thrombin to the GPIbα protein, but to rather inhibit the ristocetin-induced binding of VWF to the GPIbα protein (Ward, C. M. et al., Mocarhagin, a novel cobra venom metalloproteinase, cleaves the platelet von Willebrand factor receptor glycoprotein Ibα. Identification of the sulfated tyrosine/anionic sequence Tyr-276-Glu-282 of glycoprotein Ibα as a binding site for von Willebrand factor and α-thrombin. Biochemistry 1996, 35: 4929-4938).

It is known that the anti-GPIb antibody 4H12 inhibits the binding of thrombin to the GPIbα protein very strongly (Gralnick, U.S. Pat. No. 5,486,361 A).

The anti-GPIb antibody SZ2 (Ruan, C. et al., 1987) is in development as an inhibitory anti-platelet therapeutic (Yeung, J. & Holinstat, M., 2012).

The anti-GPIb antibody VM16d is likewise known as an antibody which inhibits the binding of thrombin to GPIb (Dubois, C. et al., Thrombin binding to GPIbα induces integrin αIIbβ3 dependent platelet adhesion to fibrin in ex vivo flowing whole blood. Thromb Haemost 2004, 91: 233-237).

As is apparent from FIG. 1, 4H12, SZ2 and VM16d inhibit the GPIbα-thrombin interaction in a concentration-dependent manner in the method according to the invention. The method is therefore suitable for detecting inhibitors of GPIb-thrombin interaction in a sample.

---

The invention claimed is:

1. A method for detecting modulators of glycoprotein Ib (GPIb)-thrombin interaction in a sample, the method comprising:
   contacting the sample with isolated glycoprotein Ibα (GPIbα) protein and with isolated thrombin; and
   determining quantitatively a complex has formation between the GPIbα protein and thrombin, wherein:

the GPIbα protein is mutated compared to a wild-type sequence of the human GPIbα protein, and contains at least amino acid residues 1-268 and has a glycine to valine substitution at position 233 and a methionine to valine substitution at position 239, the sample is not contacted with ristocetin, the thrombin and/or GPIbα protein is associated with a particulate solid phase and, the determining quantitatively a complex formation between GPIbα protein and thrombin includes measuring agglutination of the particulate solid phase, the method further comprising:

comparing the determined complex formation to a complex formation in a standard sample, wherein:

a reduced complex formation in the sample compared to the complex formation in the standard sample indicates the presence of an inhibitor of glycoprotein Ib (GPIb)-thrombin interaction in the sample, and an intensified complex formation in the sample compared to the complex formation in the standard sample indicates the presence of an activator of glycoprotein Ib (GPIb)-thrombin interaction in the sample.

2. The method of claim 1, wherein the mutated GPIbα protein has at least one more substitution from the group consisting of D235Y, D235V, and K237V.

3. The method of claim 1, wherein the thrombin and/or the GPIbα protein is associated with the solid phase via a binding partner.

4. The method of claim 3, wherein the thrombin and/or the GPIbα protein is associated with the solid phase via an antibody.

* * * * *